United States Patent
Ishikawa et al.

(10) Patent No.: US 6,366,206 B1
(45) Date of Patent: Apr. 2, 2002

(54) METHOD AND APPARATUS FOR ATTACHING TAGS TO MEDICAL AND NON-MEDICAL DEVICES

(75) Inventors: Akira Ishikawa, Royce City; Nabuo Takeda, Richardson; Suzanne I. Ahn; Steven R. Hays, both of Dallas, all of TX (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/586,077

(22) Filed: Jun. 2, 2000

Related U.S. Application Data (60) Provisional application No. 60/137,100, filed on Jun. 2, 1999.

(51) Int. Cl.⁷ .............................................. G08B 23/00
(52) U.S. Cl. ............... 340/573.1; 340/572; 340/870.17; 604/362; 604/59; 604/60
(58) Field of Search .......................... 340/573.1, 572, 340/870.17; 604/362, 59, 60

(56) References Cited

U.S. PATENT DOCUMENTS

| | | | |
|---|---|---|---|
| 4,345,253 A | 8/1982 | Hoover | 343/6.8 |
| 4,742,470 A * | 5/1988 | Juengel | 364/474 |
| 4,857,893 A | 8/1989 | Carroll | 340/572 |
| 5,057,095 A * | 10/1991 | Fabian | 604/362 |
| 5,211,129 A * | 5/1993 | Taylr et al. | 119/3 |
| 5,252,962 A | 10/1993 | Urbas et al. | 340/870.17 |
| 5,288,291 A * | 2/1994 | Teoh | 604/60 |
| 5,347,263 A | 9/1994 | Carroll et al. | 340/572 |
| 5,484,403 A * | 1/1996 | Yoakam et al. | 604/59 |
| 5,499,017 A * | 3/1996 | Beigel | 340/572 |
| 5,724,030 A * | 3/1998 | Urbas et al. | 340/870.17 |
| 5,787,174 A * | 7/1998 | Tuttle | 380/23 |
| 5,833,603 A * | 11/1998 | Kovacs et al. | 600/317 |
| 5,955,776 A | 9/1999 | Ishikawa | 257/618 |

* cited by examiner

Primary Examiner—Daniel J. Wu
Assistant Examiner—Tai T. Nguyen
(74) Attorney, Agent, or Firm—Howison, Chauza, Thoma, Handley & Arnott, L.L.P.

(57) ABSTRACT

A method and apparatus for attaching one or more transponders to medical and non-medical products to tag respective ones of the products with identifying data contained in a memory of the transponders. The one or more transponders each include a memory containing the corresponding identifying data which is emitted by the respective transponder in response to an electromagnetic signal emitted externally of the transponder. The identifying data corresponds to at least one of the respective one or more transponders and a respective product for tagging. The one or more transponders are attached to respective ones of the products to tag the products with the corresponding identifying data.

5 Claims, 5 Drawing Sheets

METHOD AND APPARATUS FOR ATTACHING TAGS TO MEDICAL AND NON-MEDICAL DEVICES

CROSS-REFERENCE TO RELATED APPLICATIONS

This application claims priority under 35 U.S.C. 119(e) to U.S. Provisional Patent Application Ser. No. 60/137,100 entitled "METHOD AND APPARATUS FOR ATTACHING TAGS TO MEDICAL DEVICES" filed Jun. 2, 1999, and is related to U.S. Pat. No. 5,955,776 entitled "SPHERICAL-SHAPED SEMICONDUCTOR INTEGRATED CIRCUIT," issued Sep. 21, 1999, and co-pending U.S. patent application Ser. No. 09/586,073 entitled "METHOD AND APPARATUS FOR TRACKING PROJECTILES," filed of even date herewith, and the following pending applications U.S. patent application Ser. No. 09/448,781 entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER,"filed Nov. 24, 1999; U.S. patent application Ser. No. 09/448,678 entitled "METHOD OF AND SYSTEM FOR IDENTIFYING MEDICAL PRODUCTS," filed Nov. 24, 1999; U.S. patent application Ser. No. 09/448,644 entitled "MONITOR FOR INTERVENTIONAL PRODUCTS," filed Nov. 24, 1999; U.S. patent application Ser. No.09/475,820 entitled "MINIATURE IMPLANTED ORTHOPEDIC SENSORS," filed Dec. 30, 1999; and U.S. Provisional Patent Application Ser. No. 06/149,799 entitled "MINIATURE PUMP-THROUGH SENSOR MODULES," filed Aug. 19, 1999, each of which are hereby incorporated by reference.

TECHNICAL FIELD OF THE INVENTION

This invention is related generally to the field of medical product inventory and control, and more particularly to a method of and system for attaching externally powered transponders to medical products for identifying, inventorying, and locating medical products, such as pills, surgical sponges, surgical instruments, and the like.

BACKGROUND OF THE INVENTION

There is a need to identify, locate, and control medical products, such as medication, surgical sponges and instruments, and other items. The need stems from patient safety and health care provider liability concerns as well as from cost concerns.

There are numerous problems with the current systems used to identify medications. Almost all methods of medication identification rely on various combinations of distinctive shapes, sizes, colors, and in some cases an alphanumerical coding system for the type and strength of medication. First, many drugs lack sufficiently distinctive markings. Printed markings are often difficult to read. There is no simple method for identifying the manufacturer of a given pill, yet most of the handbooks and catalogues require identification of the manufacturer before identification of the pill can occur. Information regarding lot number, date of manufacture, and expiration date is lost when the medication is repackaged by a pharmacy and dispensed as a prescription for the patient.

The lack of a simple system for positive identification of medications on a single dose basis leads to a very complex and costly system for dispensing medications. Automated pharmacy systems exist, but verification of which medication is dispensed remains largely a manual process. Pharmacies and nurses continue to have error rates that lead to minor and sometimes major complications for patients. The lack of positive identification for medications also leads to "copycat" medicines that look like those of a large pharmaceutical firm, but which may be inferior in quality with respect to both content and bioavailability.

Even greater problems are encountered when the patients receive their prescriptions and assume control of their medicines. Often, patients are unaware of which medications they are taking. This problem is compounded when the patient receives a large number of medications, as if often the case, especially with elderly patients. To facilitate dosing, patients place their pills in smaller containers that provide the day's medications in divided doses. Millions of dollars are spent annually having trained nurses help patients with this type of dosing. Once pills are removed from their original prescription containers, it becomes very difficult to re-sort the pills without introducing errors.

Finally, patients may not know what medicines they may have taken or in what quantity. Large amounts of nurse and physician time are expended trying to determine which medicine the patient is taking. The situation can be impossible when there are multiple manufacturers and multiple doses of the same medication.

Patients are often brought to treatment facilities without medication records and in conditions that prevent their providing an accurate medication history. Medication side effects or overdoses are often important contributors of the patient's conditions. Even when the family or nursing home staff brings the usual "bag" or list of medicines, it's not easy to determine what the patient actually took and when. Some medications may require specific "antidotes" while others require avoidance of conflicting medications. The inability of the physician to know for certain what medication(s) the patient may have taken leads to increased risks for the patient as well as increased healthcare costs for society.

Finally, there is no simple way to determine whether the medication has entered the gastrointestinal track appropriately and whether it has dissolved. Problems with swallowing may cause medications to stick in the esophagus of the patient. Certain types of foods and medications have a major impact on dissolution of medications once the patient takes them. Therefore, there is no simple and reliable method of determining whether pills taken by the patient have dissolved or not.

In addition to problems surrounding the identification of medications, sponges and instruments are on occasions inadvertently left inside the body. X-rays are often taken looking for these instruments and sponges, leading to increased operating room and anesthetic time and increased radiation to the patient and health care personnel. This can lead to pain and suffering, repeat surgery on part of the patient, and a lawsuit for the doctor and hospital. All medical items in the operating room are counted before opening the body and just before closing the body. On occasion the count is wrong mostly because of miscounting, or the instruments or other medical items having been inadvertently misplaced or discarded rather than having been left in the body. The current method of counting and finding items missing in the count prior to the closing of the patient's incision is time consuming, which means longer anesthetic time for the patient and larger hospitalization costs.

After surgery is finished in the operating room, or after procedures anywhere in the hospital or doctor's office, valuable instruments and nondisposable items are sometimes inadvertently discarded. One does not currently know the content of the trash bag without sorting through the bag, which can be not only time consuming but unsanitary and dangerous. Prior art inventory systems do not allow for the identifying material to be biocompatible or enter the body.

Some inventory systems have used identifying tags, which are secured to various items to be inventoried. These type systems typically use tags which include external identifying markings which may be read by a scanning device. Such inventory systems require that identifying tags be secured to each of various medical products for reading by the scanning device.

SUMMARY OF THE INVENTION

The present invention disclosed and claimed herein, in one aspect thereof, comprises a method of attaching one or more transponders to medical and non-medical products to tag units of the products with identifying data contained in a memory of the transponders. The one or more transponders each include a memory containing the corresponding identifying data which is emitted by the respective transponder in response to an electromagnetic signal emitted externally of the transponder. The identifying data corresponds to at least one of the respective one or more transponders and a respective product for tagging. The one or more transponders are attached to respective ones of the products to tag the products with the corresponding identifying data. The methods of attaching include at least one from the group of inserting, implanting, tissue glueing, epoxy glueing, laminating, sewing, hot pressing, shrink wrapping, vacuum wrapping, soldering, encasing in plastic, rolling into, molding, strapping, stamping, retrofitting, embossing, hooking, attaching by VELCRO™ or the like, intertwining clusters of balls, attaching by TEFLON™, meshing, emulsifying, suspending, floating or mixing in liquids, gases, slurries and the like, swaging, electrostatic bonding, embedding by polymer polymerization, embedding by pulse plasma polymerization, encased within a liposome for oral, intravenous, transdermal, subcutaneous or other means of delivery, contained integrally within the structure of a microspherical semiconductor serving other purposes, for example, a drug delivery reservoir, biosensor, temperature sensor and the like, and entrapping the transponder segments with an attachment layer.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
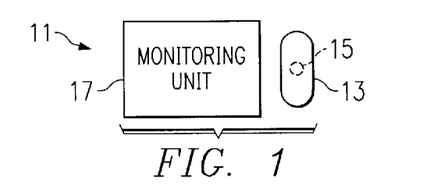
FIG. 1 illustrates a pictorial view of a system made according to a disclosed embodiment.

Referring now to FIG. 1, there is illustrated a system which is designated generally by the numeral 11. The system 11 includes a pill 13 having an almost microscopic externally powered transponder 15 embedded therein. Preferably, the transponder 15 is attached to the pill by being mixed into the medication encapsulated in the case of the pill 13. The pill 13 is any of several well known types of oral medication in pill form. As will be described in detail hereinafter, transponder 15 includes a memory containing identifying data for the pill 13. The identifying data contains such information as the identification of the medication, the dosage of the medication contained in the pill 13, the identity of the manufacturer of the pill 13, the date of manufacture of the pill 13, and/or other information, such as a unique serial number for the pill 13. Other data which may be written into the memory include patient and doctor information, date of issuance of the pill, and other patient medical information helpful to those entities that read the contents of the memory.

The data in the memory of transponder 15 is read by an external monitoring unit, indicated generally at 17. Monitoring unit 17 may be a hand-held device or it may be a fixed device in a hospital, doctor's office, pharmacy, or other facility. As will be explained in detail hereinafter, monitoring unit 17 provides power to and interrogates transponder 15, and displays or records the data read from transponder 15. Monitoring unit 17 can be used to obtain identifying information for pill 13 outside of a body or inside the body after pill 13 has been ingested. Also, monitoring unit 17 can obtain identifying information from transponder 15 after pill 13 has dissolved in the body, which is particularly useful in overdose situations. The transponder 15 may have a sensor that detects moisture or change in pH to determine whether the pill 13 has dissolved and exposed the transponder 15 to the environment of the gut.

Figure 2:
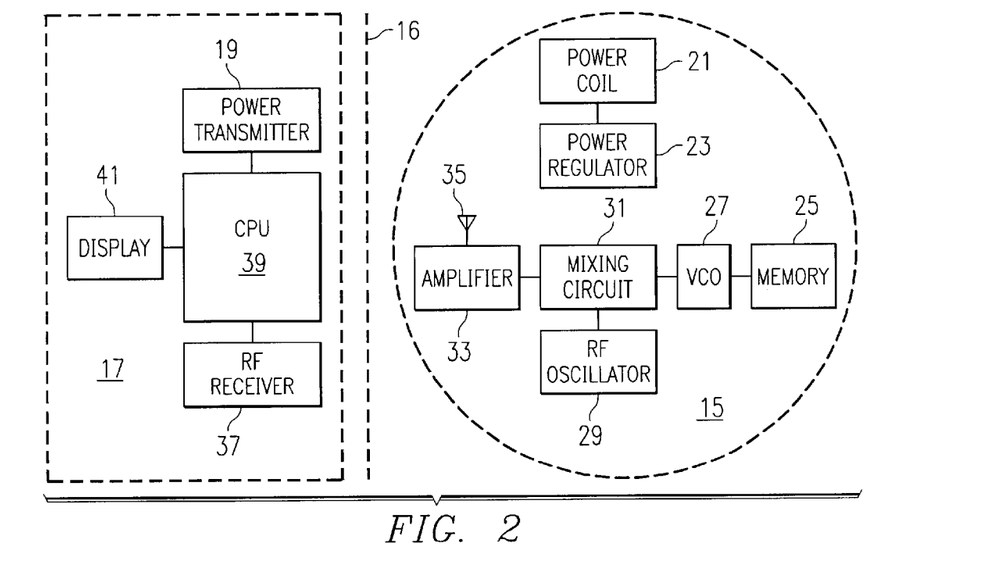
FIG. 2 illustrates a block diagram of the system.

Referring now to FIG. 2, there is illustrated a simplified block diagram of a system of the present invention. The transponder 15 is a "passive" transponder preferably of the type disclosed generally in U.S. Pat. No. 5,347,263 by Carroll et al. entitled "Electronic Identifier Apparatus And Method Utilizing A Single Chip Microcontroller And An Antenna Coil," issued Sep. 13, 1994, U.S. Pat. No. 5,252,962 by Urbas et al. entitled "System Monitoring Programmable Implantable Transponder," issued Oct. 12, 1993, U.S. Pat. No. 4,857,893 by Carroll entitled "Single Chip Transponder Device," issued Aug. 15, 1989, and U.S. Pat. No. 4,345,253 by Hoover entitled "Passive Sensing And Encoding Transponder," issued Aug. 17, 1982, the disclosures of which are hereby incorporated by reference. Passive transponders do not include an onboard power source such as a battery. Rather, passive transponders receive power from an external source.

The external source, monitoring unit 17, illustrated as external to the body by being left of a dashed line 16 (the transponder 15 being internal to the body, i.e., to the right of the dashed line 16), includes a power transmitter 19. The power transmitter 19 directs electromagnetic radiation at transponder 15. The electromagnetic radiation generated by the power transmitter 19 induces current in a power coil 21 carried by transponder 15. A power regulator 23 rectifies and regulates the current induced in power coil 21 to provide a relatively constant DC voltage level of about three volts to the circuitry of transponder 15. However, larger or smaller voltages can be used according to the specific design constraints of the application.

Transponder 15 includes the memory indicated generally at 25. Memory 25 is preferably an Electronically Erasable Programmable Read-Only Memory (EEPROM) of the type well known in the art. As is known to those skilled in the art, memory 25 includes a programmable memory array, address decoders, and appropriate output buffers, all as is well known to those skilled in the art. Memory 25 also includes clocking and sequencing means for outputting the data stored therein.

Memory 25 is programmed with identifying data for the pill 13. Typically, the identifying data is programmed into memory the 25 by the manufacturer of the pill 13. The identifying information includes the identity of the drug or medication of the pill 13 and the dosage level of the pill 13. The data may also include such information as lot number, date of manufacture, location of manufacture, or any other information the manufacturer may desire or be required to include in the memory 25, such as a unique serial number so that each pill 13 can be separately identified even from identical pills of the same lot. The size of the memory 25 is preferably large enough to contain the data.

Transponder 15 includes onboard data communications circuitry which is essentially the modulation/demodulation site for data and signals. The output from the memory 25 is coupled to the input of a voltage controlled oscillator (VCO) 27. The VCO 27 produces a signal the frequency of which is related to the input voltage. The output for memory 25 is either a high voltage level or a low voltage level. Thus, VCO 27 thus provides frequency-shift keying (FSK) to the data received from memory 25. As is well known to those skilled in the art, higher transmission rates can be obtained using phase-shift keying (PSK), quadrature amplitude modulation (QAM), or other modem technologies.

The FSK signal produced by VCO 27 modulates an radio frequency (RF) signal produced by an RF oscillator 29. The modulation occurs in a mixing circuit 31. The modulated output from mixing circuit 31 is output to an RF amplifier 33. Amplifier 33 amplifies the signal and outputs the amplified signal to an antenna 35. Antenna 35 may be a separate antenna carried by transponder 15, or it may be power coil 21.

Antenna 35 of transponder 15 radiates the data modulated RF signal exterior of transponder 15. The data modulated RF signal is received by a radio frequency receiver 37, which is part of monitoring station 17. The RF receiver 37 is a conventional receiver and it preferably includes an onboard modem for demodulating the signal. The RF receiver 37 is coupled to a central processing unit 39, which decodes the data received from transponder 15. Monitoring unit 17 includes a display 41 connected to central processing unit 39. Display 41 may be a simple LED display. Alternatively, display 41 may be a video monitor with elaborate graphical features.

Figure 3:
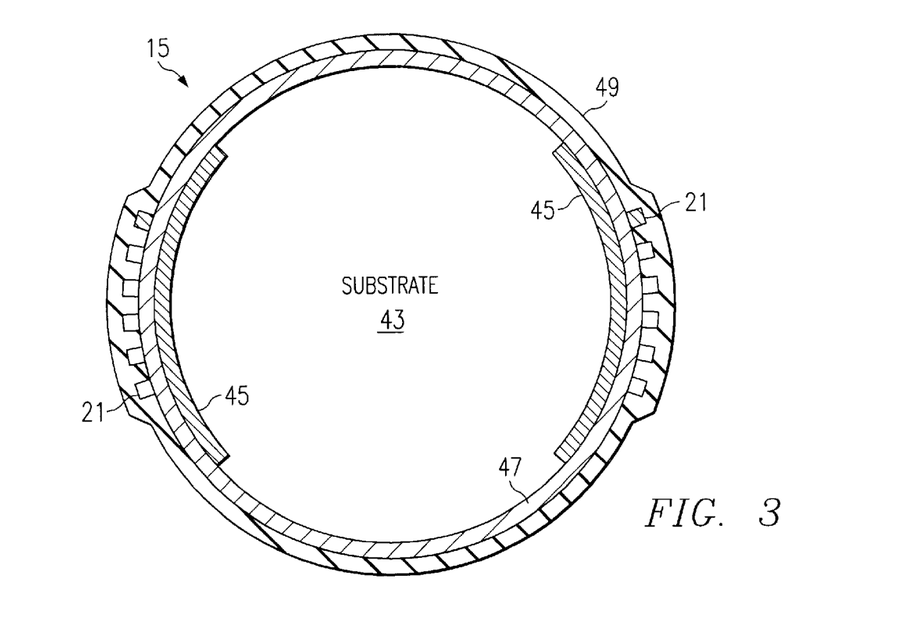
FIG. 3 illustrates a sectional view of the transponder of a disclosed embodiment.

Referring now to FIG. 3, transponder 15 preferably comprises a substantially spherical semiconductor device on which an integrated circuit has been formed. Such a spherical-shaped integrated circuit semiconductor device (sometimes referred to herein as a "ball") is described in a commonly assigned U.S. Pat. No. 5,955,776 by Ishikawa entitled "Spherical Shaped Semiconductor Integrated Circuit," issued Sep. 21, 1999, the disclosure of which is hereby incorporated by reference.

Referring further to FIG. 3, there is illustrated the transponder 15 built on a substantially spherical semiconductor substrate 43, which may be doped P-type or N-type in accordance with the particular requirements of the fabrication process. Semiconductor circuitry indicated generally at 45 resides on substrate 43. Circuitry 45 includes the elements illustrated in FIG. 2, including power coil 21, power regulator 23, memory 25, VCO 27, RF oscillator 29, mixing circuit 31, and amplifier 33, as well as other circuitry. Substrate 43 and circuitry 45 are covered with an insulating layer 47. Insulating layer 47 is preferably formed of silicon dioxide or phosphosilicate glass.

Power coil 21 is formed of helically wrapped windings over insulating shell 47. Power coil 21 may be fabricated from a deposited layer of aluminum that is patterned and etched using conventional semiconductor fabrication techniques. The actual number of individual windings of power coil 21 may differ from those shown, and may be far greater than the six shown in FIG. 3.

Transponder 15 is coated with or encapsulated in a layer 49 of a biologically inert material such as phosphosilicate glass or TEFLON™. The coating could also consist of a pulse plasma polymerization TEFLON™. Coating 49 can withstand the acidity of the stomach to a very low pH level and it is not subject to the enzymatic actions of the digestive tract. Also, coating 49 is inert to and does not react with the material of pill 13. Transponder 15 is substantially spherical and preferably about 1 mm in diameter. The very small size of transponder 15 enables it to be embedded in a pill 13 without increasing substantially the overall volume of the pill. However, the transponder 15 should be made large enough not to be absorbed through the microvilli in the lining of the digestive tract.

Figure 4:
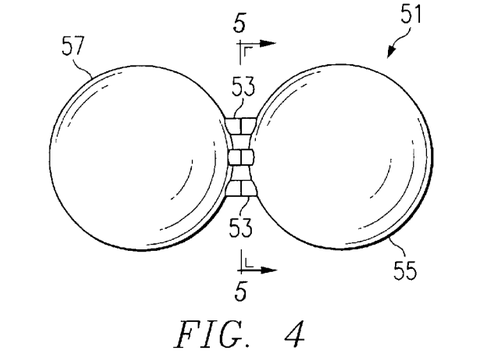
FIG. 4 illustrates a view of an alternative embodiment of the transponder.

Referring now to FIG. 4, there is illustrated an alternative embodiment of a transponder of the present invention, which is designated generally by the numeral 51. Transponder 51 comprises two separate balls interconnected by metal contacts or solder bumps 53. The balls of transponder 51 include a circuit ball 55 and a memory ball 57. Circuit ball 55 and memory ball 57 are constructed in the manner illustrated with respect to FIG. 3. Circuit ball 55 preferably includes a substantially spherical semiconductor substrate upon which resides the power coil 21, power regulator 23, VCO 27, RF oscillator 29, mixing circuit 31, and amplifier 33 of FIG. 2. However, semiconductor substrates of other shapes may be used. Memory ball 57 similarly preferably includes a substantially spherical semiconductor substrate upon which resides memory 25 of FIG. 2. By clustering the memory and circuit balls 55 and 57 in the embodiment of FIG. 4, the size of memory available to the transponder 51 may be increased greatly. Transponder 51 is encapsulated in a biologically inert material such as phosphosilicate glass or TEFLON™.

Figure 5:
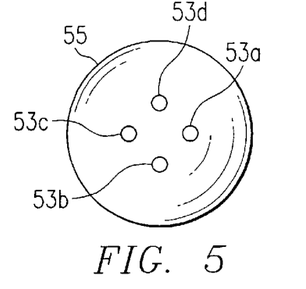
FIG. 5 illustrates a view taken along line 5—5 of FIG. 4.

Referring now to FIG. 5, there is illustrated a cross section view of the interface contacts of the circuit ball taken along the line 5—5 of FIG. 4. In this embodiment, four contacts 53a, 53b, 53c and 53d are located between the memory ball 57 and the circuit ball 55. The contacts 53a and 53b may be power contacts, such as a positive 3.0 volts and ground, which can be passed from the circuit ball 55 to the memory ball 57 by conductors on its surface using two of a group of similar contacts (designated collectively by numeral 53 in FIG. 4). The contacts 53c and 53d may be data and control contacts for data and control communications between the circuit ball 55 and memory ball 57. Note that this embodiment is not limited to two interconnected balls or a segregation of specific functions to designated balls, but may comprise any number of balls interconnected to provide the assembly of desired functions.

Figure 6:
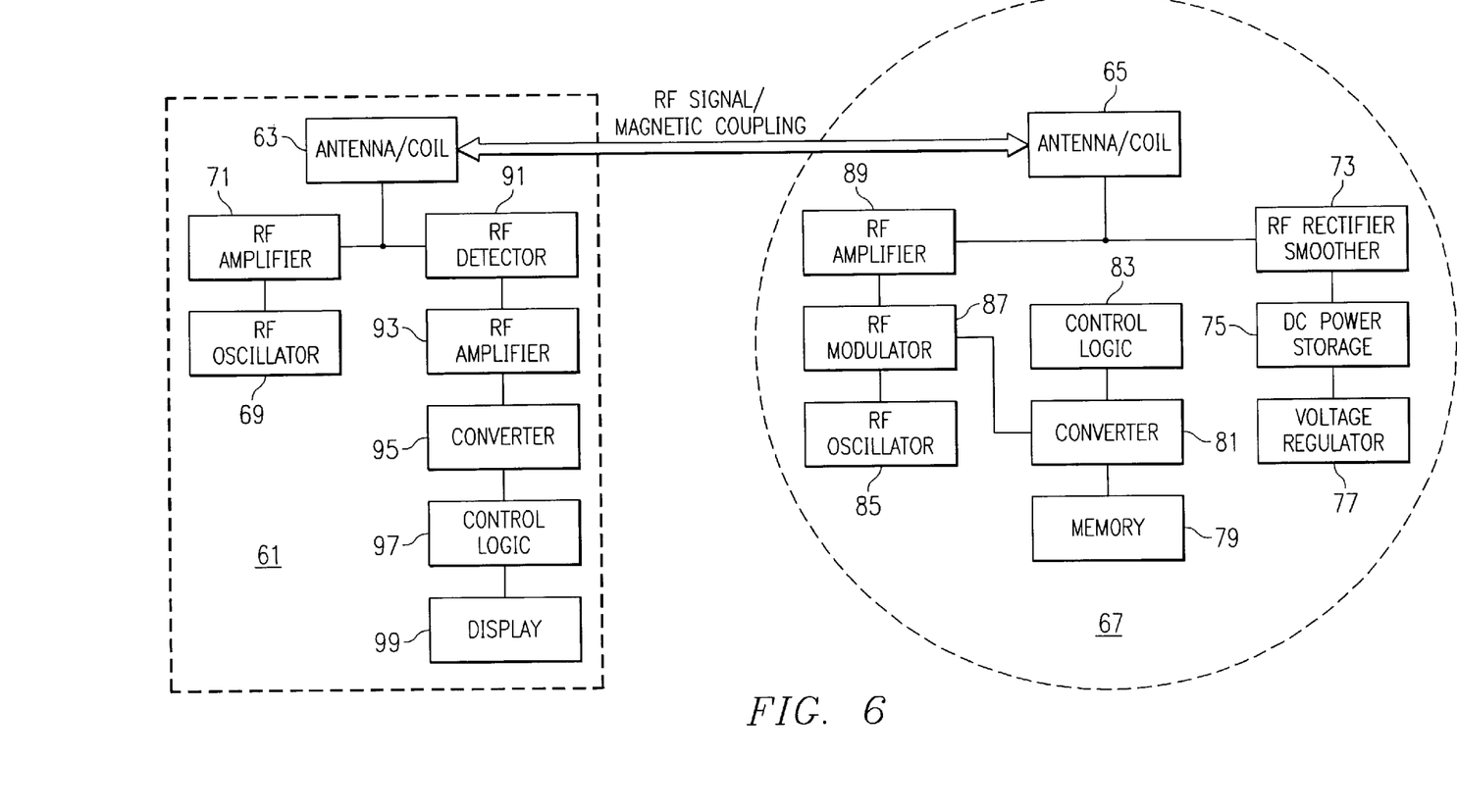
FIG. 6 illustrates a block diagram of an alternative system.

Referring now to FIG. 6, there is illustrated an alternative embodiment of the disclosed architecture. A monitoring unit 61 (similar to monitor unit 17) includes an antenna/coil 63 that transmits RF power to an antenna/coil 65 of ball transponder 67 (similar to transponder 15). Power is transported either by RF radiation or by magnetic coupling between antenna/coil 63 and antenna/coil 65. Monitoring unit 61 generates RF power with an RF oscillator 69 coupled to an RF amplifier 71. RF amplifier 71 is coupled to antenna/coil 63.

The RF power received at antenna/coil 65 of transponder 67 is rectified and smoothed by an RF rectifier smoother 73 which is coupled to antenna/coil 65. RF rectifier smoother 73 converts RF energy to a DC voltage source. DC power is stored in a DC storage unit 75, which preferably includes a capacitor. The capacitor of DC power storage unit 75 may be included in the smoother portion of RF rectifier smoother 73. A voltage regulator 77 is coupled to DC power storage unit 75. Voltage regulator 77 makes the DC voltage powering transponder 67 stable for any condition or distance between monitoring unit 61 and transponder 67. Voltage regulator 77 supplies DC voltage to all circuits of transponder 67 in a manner well known to those skilled in the art.

Transponder 67 includes a non-volatile memory 79, which is programmed with identifying information. The output from memory 79 is converted to a frequency signal by a converter 81. Control logic 83 controls converter 81. Control logic 83 may control the activity of all the circuits on transponder 67, though only a connection to converter 81 is shown in FIG. 6. Control logic 83 may be a signal processor.

To transit information, transponder 67 includes an RF oscillator 85. The frequency of RF oscillator 85 is preferably not the same as the frequency generated by RF oscillator 69 of control unit 61. The RF signal produced by RF oscillator 85 is modulated with the signal produced by converter 81 in an RF modulator 87. The modulated RF signal is amplified by an RF amplifier 89, which is coupled to antenna/coil 65. Transponder 67 may operate under AM, FM, PM, or other digital modulation methods.

The information transmitted from transponder 67 is received at antenna coil 63 of monitoring unit 61. The RF signal received at antenna/coil 63 is detected by an RF detector 91 and amplified by an RF amplifier 93. The amplified signal is converted to a digital signal by a converter 95, which is an A/D converter or a demodulator. Converter 95 is coupled to control logic 97, which processes the data received from transponder 67 and controls a display 99 and other electrical circuitry of monitoring unit 61. Display 99 is either a display to a human operator or it may be an interface to other equipment.

In addition to pills, the transponder 15 of the present disclosure may be used to tag any medical product or device, or non-medical product or device. For example, the transponder 15 may be affixed or otherwise attached to a surgical sponge. The transponder 15 would contain data to identify the sponge. Before closing the patient's body at the site of the surgery, the site would be scanned with the monitoring unit 17. If a sponge ball transponder 15 were to respond, the sponge could be located and removed. Other medical items, such as surgical instruments, may be similarly tagged with the ball transponder 15 of the present disclosure. The instruments could be scanned before surgery to generate an inventory. At the conclusion of the surgery, the surgical suite could be scanned to account positively for all items in the inventory.

Figure 7:
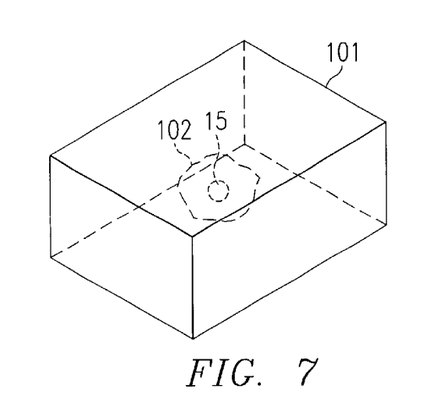
FIG. 7 illustrates a perspective view of a sponge with a transponder which has been inserted into a central portion of the sponge.

Referring now to FIG. 7, there is illustrated a perspective view of a sponge 101 with a transponder 15 which has been inserted in a central portion of the sponge 101. The transponder 15 is inserted into the central region of the sponge 101 such that the transponder 15 will not be ejected therefrom during use of the sponge 101. In some embodiments, the transponder 15 may be embedded in a retaining material 102, such as an epoxy slug, plug, a plastic mass, full or partial coating of sponge material, or the like, which is too large to be ejected from the sponge 101 during use.

Figure 8:
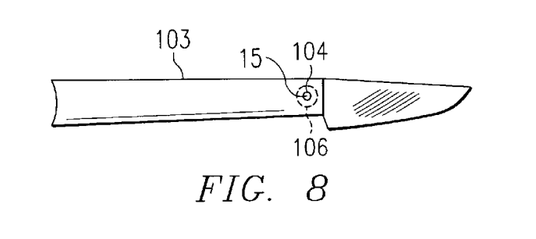
FIG. 8 illustrates a side elevation view of a scalpel with a transponder embedded in the scalpel.

Referring now to FIG. 8, there is illustrated a side elevation view of a scalpel 103 with a transponder 15 attached to the scalpel 103. The transponder 15 is attached to the scalpel by being embedded therein, preferably by a stamping or swaging process which causes a portion 106 of the material of the scalpel to extrude above an outwardly disposed portion of the transponder 15. Thus, a transmission portal 104 extends adjacent to the transponder 15 having open linear length which is smaller than the diameter of the transponder 15. Preferably, the transponder 15 is spherical and the transmission portal 104 is round. The transmission portal is formed by partially extruding the material 106 of the scalpel 103 over the transponder 15.

Figure 9:
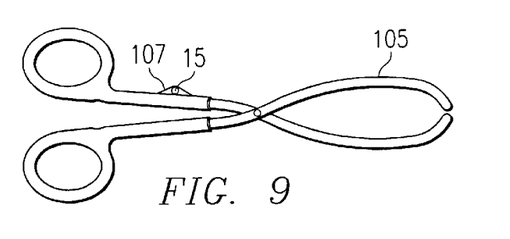
FIG. 9 illustrates a top view of a surgical tool with a transponder attached to the exterior of the tool.

Referring now to FIG. 9, there is illustrated a top view of a surgical tool 105 with a transponder 15 attached to the exterior of one of the handles of the tool (e.g., clamp, tongs, etc.) 105. The transponder 15 has been attached to the tool 105 by being embedded in an attachment layer 107 placed on the surface of the handle of the tool 105. The attachment layer 107 may be an adhesive layer, such as a layer of epoxy, a strip of tape, solder, or such other laminate member.

Figure 10:
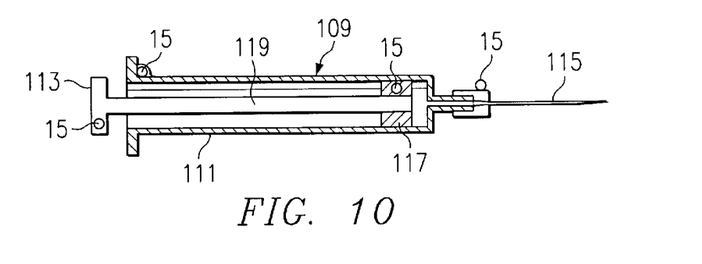
FIG. 10 illustrates a side elevation view of a syringe and a hypodermic needle with transponders attached to various components of the syringe and the hypodermic needle.

Referring now to FIG. 10, there is illustrated a side elevation view of a syringe 109 and a hypodermic needle 115, with various transponders 15 attached to various components of the syringe 109 and the hypodermic needle 115. Each of the separable components of the syringe 109 has a corresponding one of the transponders 15 attached by being embedding in either the material from which such components are made or an adhesive layer, such as a layer of epoxy. Scanning of the transponders 15 results in an identification code being transmitted by respective units of the transponders 15. The syringe comprises a barrel 111 within which is received a plunger assembly 113. The plunger assembly 113 includes a shank 119 and a seal element 117, which sealingly engages within the barrel 111. Each of the barrel 111, the seal element 117 and the shank 119 has a corresponding transponder 15 attached thereto, such that inadvertent disassembly of the syringe 109 into the various components thereof will not result in unaccounted for materials in an operating room. The shank 119 is preferably made as one-piece with the thumb portion of the plunger assembly 113, but if such are separable, separate transponders 15 are then preferably used for each such separable component of the plunger assembly 113.

Figure 11:
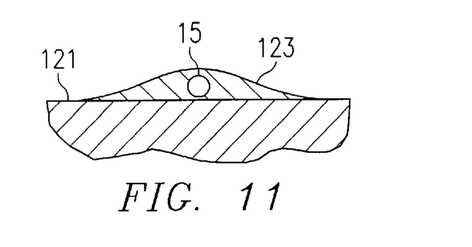
FIG. 11 illustrates a schematic diagram depicting a transponder attached to a surface.

Referring now to FIG. 11, there is illustrated a schematic diagram depicting a transponder 15 attached to the exterior of a surface 121 by an attachment member 123. The attachment member 123 may be a laminate layer of an adhesive, such as epoxy or the like. In other embodiments, adhesively backed tapes, hot melt glues, plastic weldments, solder, cold fused materials and the like may be used for attachment member 123, depending upon the type material of which the surface 121 is made.

Figure 12:
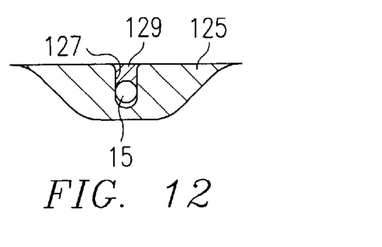
FIG. 12 illustrates a schematic diagram depicting a transponder attached to a mounting member by securing the transponder within the mounting member with a securement member.

Referring now to FIG. 12, there is illustrated a schematic diagram depicting a transponder 15 attached to a mounting member 125. The transponder 15 is located in a blind hole 127, and then secured therein with a plug defined by an attachment member 129. The attachment member 129 may be provided by various materials, such as those listed above for the attachment member 123, which is typically determined by the type of material of which the mounting member 125 is formed. In other embodiments, such as when the mounting member 125 is formed of a thermoplastic, the attachment member 129 may be formed by a sonic welding process, whereby the material of the mounting member 125 is plastically deformed by mechanical vibration to retain the transponder 15 within the mounting member 125.

Figure 13:
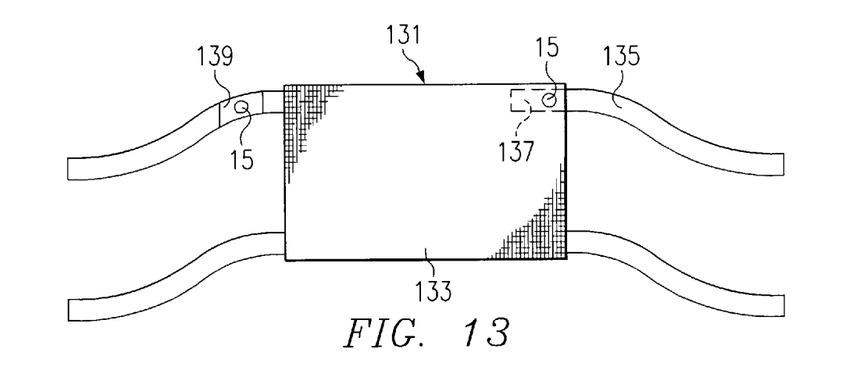
FIG. 13 illustrates a side elevation view of a surgical mask with transponders attached to various components of the surgical mask.

Referring now to FIG. 13, there is illustrated a side elevation view of a surgical mask 131 having a filter region 133 and tie straps 135. Transponders 15 are attached to the mask 131 by being woven into respective ones 137 and 139 of the filter regions and the tie straps 135 of the surgical mask 131.

Figure 14:
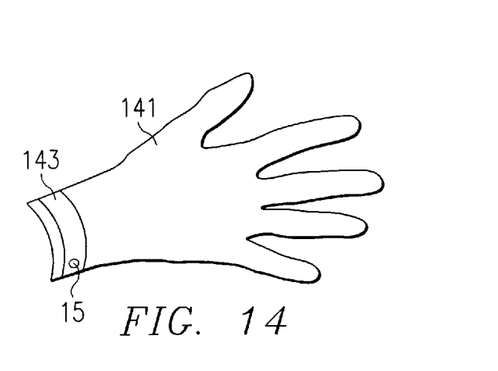
FIG. 14 illustrates a top view of a surgical glove with a transponder attached to the glove.

Referring now to FIG. 14, there is illustrated a top view of a surgical glove 141 with a transponder 15 attached to a wrist region 143 the glove 141. The transponder 15 may be embedded in a strip defining the wrist region 143, which is molded into the glove 141.

Figure 15:
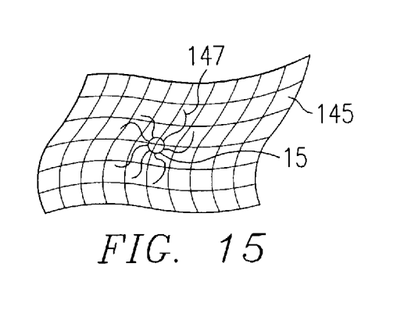
FIG. 15 illustrates a top view of a piece of gauze with a transponder attached to the gauze by being woven into the gauze and the transponder having hook members for retaining the transponder within the gauze.

Referring now to FIG. 15, there is illustrated a top view of a piece of gauze 145, with a transponder 15 attached to the gauze 145 by being woven into the gauze 145. The transponder 15 is embedded in hook members 147, which are woven into the gauze 145. The hook members 147 are preferably made of fabric, but in other embodiments, metal wires or strips may be used for the hook members 147. In some embodiments, polymer chains may provide the hook members 147. In yet other embodiments, the transponder 15 may also be included in a laminated strip, which is woven into the gauze 145.

Figure 16:
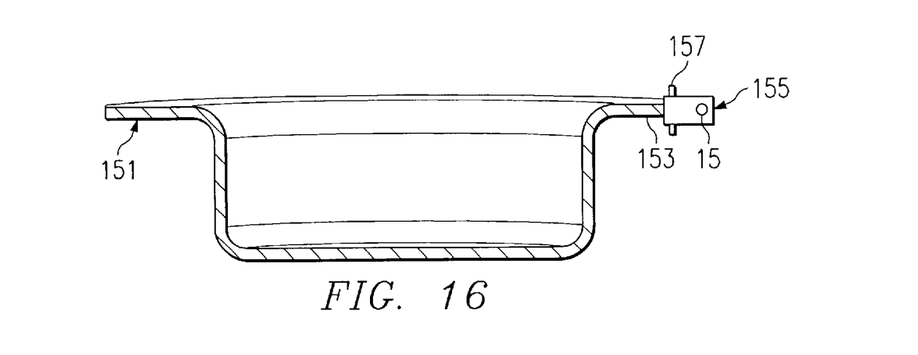
FIG. 16 illustrates a sectional view of a tray, with a transponder assembly attached to a rim of the tray with a mechanical fastener.

Referring now to FIG. 16, there is illustrated is a sectional view of a surgical tray 151 having a lip 153 to which a transponder 15 is attached by being mechanically secured thereto. The transponder 15 is retained within a transponder assembly 155, which secured to the rim 153 of the tray 151 with a fastener 157, such as a rivet, a bolt, a screw, or such other type of mechanical fastener.

Figure 17:
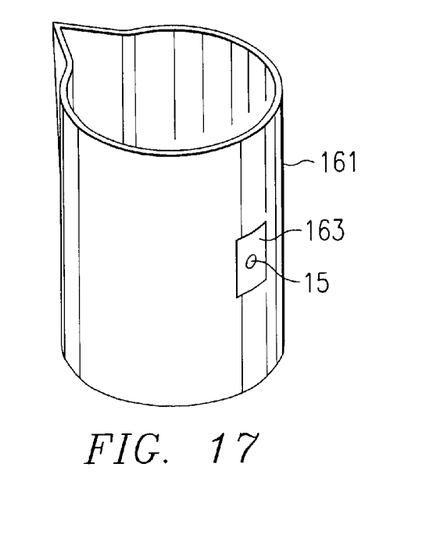
FIG. 17 illustrates a side elevation view of a plastic bag, with a transponder attached to the bag by a laminate member.

Referring now to FIG. 17, there is illustrated a side elevation view of a plastic bag 161, with a transponder 15 attached to the bag 161 by a laminate member 163. Preferably, the laminate member 163 is a strip of tape secured to the bag 161 by an epoxy adhesive, or the like.

Figure 18:
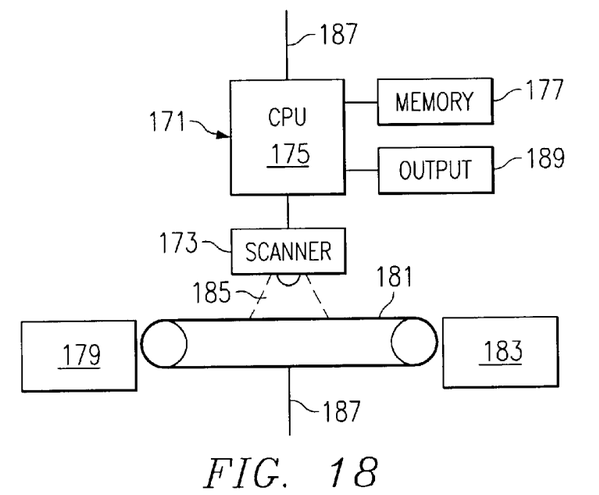
FIG. 18 illustrates a schematic diagram of an apparatus for monitoring inventory of surgical items in an operating room.

Referring now to FIG. 18, there is illustrated a schematic diagram of an apparatus 171 for monitoring inventory of surgical items in an emergency room. The apparatus 171 includes a scanner 173, which is operable for causing the identifying data of the various items in the operating room to be emitted by the corresponding transponders 15. The scanner 173 is operably connected to a CPU 175 and memory 177 for comparing items input into the operating room with those being removed from the operating room. A first staging area 179, a conveyor belt 181 and a second staging area 183 may be provided for moving the surgical items beneath the scanner 173. The first staging area 179 may be used for staging items being input beneath the scanner 173 for checking items into the operating room. After use, the miscellaneous surgical items will then be staged on the area 183 for passing beneath the scanner 173 to check the items out from the operating room. Preferably, a physical barrier 187 extends between the staging areas 179 and 183 to prevent items from inadvertently passing therebetween. In some embodiments, the physical barrier 187 may be an operating room wall, and items will be checked into and out of the operating room inventory by passing beneath the scanning region 185 of the scanner 173. An output member 189 is also preferably provided to maintain a permanent tracking record of items checked into and out of the operating room inventory. The output member 189 may be provided by a printer, a hard drive, or other storage media.

Figure 19:
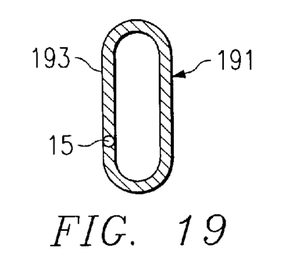
FIG. 19 illustrates a longitudinal section view of a pill case with a transponder molded into an interior of the case.

Referring to FIG. 19, there is illustrated a longitudinal section view of a pill 191 having a case 193 with a transponder 15 secured to the interior of the case 193. The transponder 15 has been encapsulated, or molded, into a sidewall of the case 193.

Figure 20:
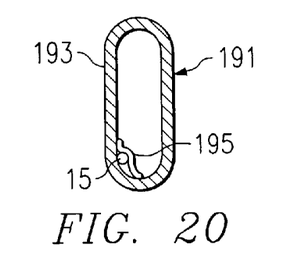
FIG. 20 illustrates a longitudinal section view of a pill case with a transponder attached to an interior of the case by an attachment layer.

Referring now to FIG. 20, there is illustrated a longitudinal section view of the pill 191 having a case 193, with a transponder 15 attached to an interior of the case 193. The transponder 15 has been attached to the case 193 by an attachment layer 195, which provides a layer for securing to the interior of the case 193 with the transponder 15 encapsulated therebetween.

Figure 21:
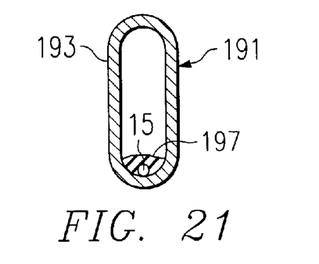
FIG. 21 illustrates a longitudinal section view of a pill case with a transponder attached to an interior of the case by encapsulating in an attachment layer.

Referring now to FIG. 21, there is illustrated a longitudinal section view of the pill 191 with a case 193 having a transponder 15 attached to an interior of the case 193. The transponder 15 has been attached to the case 193 by being embedded within an attachment layer 197, which preferably is an adhesive which is cured to secure the transponder 15 within the case 193.

Other attachment methods may be use for securing the transponders 15, and the like, to various medical products. The transponders 15 are preferably almost microscopic in size and spherical in shape. The methods of attaching include at least one from the group of inserting, implanting, tissue glueing, epoxy glueing, glueing, laminating, sewing, hot pressing, shrink wrapping, vacuum wrapping, soldering, encasing in plastic, rolling into, molding, strapping, stamping, retrofitting, embossing, hooking, attaching by VFLCRO™ or the like, intertwining clusters of balls, attaching by TEFLON™, meshing, emulsifying, suspending, floating or mixing in liquids, gases, slurries and the like, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, for example, a drug delivery reservoir, biosensor, temperature sensor, and the like, and entrapping the transponder segments with an attachment layer. The transponders 15, preferably balls, may be attached to various metals, including gold, silver, stainless steel, titanium, Nitinol and lead, and to various materials, including gauze, sponges, rubber gloves, paper, polyethylene, and all other types of plastic, silicone rubber, and all other types of rubber and cloth.

From the foregoing, it may be seen that the disclosed architecture overcomes the shortcomings of the prior art. An almost microscopic, spherical, integrated circuit transponder or ball is imbedded in pills (medication in pill, capsule, or any other ingested form), in transdermal patches and liposome-based delivery systems, and other medical items, to provide a means of positive identification. The ball contains specific information in each pill such as the type of medication, its authenticity, dosage, manufacturer, lot number, date of manufacture, and date of expiration. Because of its size and its biologically inert properties, the ball is undigested and unaffected by the acid environment of the stomach. A small antenna on the ball allows it to send and receive RF signals (RF transponder). The ball is eliminated from the body with normal bowel movements, or detached, in the case of transdermal delivery systems, or surgically removed, in the case of subcutaneous liposome delivery systems.

The positive, discrete identification of commercially manufactured medications at the single dosage level will improve many pharmaceutical activities including inventory control, distribution, prescription filling and the actual dispensing of medications to the patient. It will also have a major impact on medical practice by permitting health care workers to identify positively which medications the patient has taken and how many pills remain within the patient's body. This information can be obtained from patients who are not able to provide a medication history on their own (e.g. forgetful, memory-impaired, or unconscious patients). The RF from each pill would also provide some general information about its location within the gastrointestinal tract, from the esophagus through the colon.

The cost of the ball transponders of the present disclosure is sufficiently low and affordable to allow its inclusion in the smallest unit of medication. Simple RF sensing devices will be used to interrogate the transponder within the pill and identify it beyond a level currently available with any existing system.

Pills for animals would be coded similarly to provide the same benefits. It would also provide a robust method of identifying which medications are for human or for veterinary use.

If every medical item and supply in the hospital or doctor's office is tagged, the trash cans or trash bags can be scanned. The scanning can also be done for billing purposes. Hospitals now use bar codes for billing supply items. The ball tags would be incorporated into the medical items, so that the items can be scanned even after the packaging for the item has been opened and discarded. Because the ball ID tags are small and inexpensive, they can be inserted into or attached to every medical item.

Notably, the disclosed tagging method and apparatus are not restricted to medical applications, but also has application in non-medical environments. For example, the scanning (or reading) system of FIG. 18 has application in other environments where objects can be identified with information stored in an attached transponder. An airport security system may implement luggage or article tagging to account for and associate all pieces transported via the airlines. Similarly, where products are transported by mail, such as boxes or letters, the disclosed method and apparatus are coupled with the scanning (or reading system) may be used to tag and, therefore identify with a sender, each piece of mail being transported. Further examples benefitting from the disclosed method and apparatus include the tagging of testing samples which provide visual privacy by not needing to include patient information in the form of text on a sample, while still maintaining association of essential data stored in the transponder. Food products, seeds, animals, biological products, tools, clothing, toys, and building products are examples which can benefit from the disclosed tagging method and apparatus. Virtually any object large enough for the spherical transponder to be attached may benefit from the disclosed tagging method and apparatus. Additionally, although of spherically shaped semiconductors are described herein, devices of other shapes and materials may be used, such as flat semiconductors, semiconductors of other three-dimensional shapes, including square, rectangular, conical and other non-spherically shaped semiconductors, and materials other than semiconductors and conventional semiconductors.

Although the preferred embodiment has been described in detail, it should be understood that various changes, substitutions and alterations can be made therein without departing from the spirit and scope of the invention as defined by the appended claims.

What is claimed is:

1. A medical product, comprising:

an item for use as a medical product;

one or more transponders secured to said item, said one or more transponders including a memory containing identifying data for said item, signal circuitry for transmitting said identifying data in an electromagnetic signal, and power circuitry for powering said signal circuitry in response to an external electromagnetic signal, wherein each of said one or more transponders further comprises:

a semiconductor substrate;

wherein said signal circuitry resides on or in said semiconductor substrate for modulating an RF signal with said data contained in said memory; and, wherein said power circuitry resides on or in said semiconductor substrate for powering said signal circuitry in response to said external electromagnetic signal; and a structure securing said one or more transponders to said item, where said structure is provided by at least one of the group of inserting, implanting, tissue glueing, epoxy glueing, glueing, laminating, sewing, hot pressing, shrink wrapping, vacuum wrapping, soldering, encasing in plastic, rolling into, molding, strapping, stamping, retrofitting, embossing, hooking, attaching by VELCRO™, intertwining clusters of balls, attaching by TEFLON™, meshing, emulsifying, suspending, floating or mixing in liquids, gases, slurries, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, including one of drug delivery reservoir, biosensor and temperature sensor; and entrapping the transponder segments with an attachment layer.

2. A medical product, comprising:

an item for use as a medical product;

one or more transponders secured to said item, said one or more transponders including a memory containing identifying data for said item, signal circuitry for transmitting said identifying data in an electromagnetic signal, and power circuitry for powering said signal circuitry in response to an external electromagnetic signal, wherein said one or more transponders comprise a circuit ball electrically coupled to said memory, said circuit ball comprising a substantially spherical substrate, and signal circuitry residing on or in said substrate for modulating an RF signal with data contained in said memory; and wherein said power circuitry powers said RF modulating signal circuitry; and a structure securing said one or more transponders to said item, where said structure is provided by at least one of the group of inserting, implanting, tissue glueing, epoxy glueing, glueing, laminating, sewing, hot pressing, shrink wrapping, vacuum wrapping, soldering, encasing in plastic, rolling into, molding, strapping, stamping, retrofitting, embossing, hooking, attaching by VELCRO™, intertwining clusters of balls, attaching by TEFLON™, meshing, emulsifying, suspending, floating or mixing in liquids, gases, slurries, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, including one of drug delivery reservoir, biosensor and temperature sensor; and entrapping the transponder segments with an attachment layer.

3. The medical product of claim 2, wherein said memory resides on or in said circuit ball.

4. A medical product, comprising:

an item for use as a medical product;

one or more transponders secured to said item, said one or more transponders including a memory containing identifying data for said item, signal circuitry for transmitting said identifying data in an electromagnetic signal, and power circuitry for powering said signal circuitry in response to an external electromagnetic signal, wherein said memory resides on or in a substantially spherical memory ball electrically coupled to a substantially spherical circuit ball; and a structure securing said one or more transponders to said item, where said structure is provided by at least one of the group of inserting, implanting, tissue glueing, epoxy glueing, glueing, laminating, sewing, hot pressing, shrink wrapping, vacuum wrapping, soldering, encasing in plastic, rolling into, molding, strapping, stamping, retrofitting, embossing, hooking, attaching by VELCRO™, intertwining clusters of balls, attaching by TEFLON™, meshing, emulsifying, suspending, floating or mixing in liquids, gases, slurries, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, including one of drug delivery reservoir, biosensor and temperature sensor; and entrapping the transponder segments with an attachment layer.

5. An apparatus for attaching identifying data to an object, comprising:

one or more substantially spherical transponders attached to the object, and each having a memory containing the data associated with the object; and a structure attaching said one or more transponders to the object by at least one from the group of inserting, implanting, tissue glueing, epoxy glueing, glueing, laminating, sewing, hot pressing, shrink wrapping, vacuum wrapping, soldering, encasing in plastic, rolling into, molding, strapping, stamping, retrofitting, embossing, hooking, attaching by VELCRO™, intertwining clusters of balls, attaching by TEFLON™, meshing, emulsifying, suspending, floating or mixing in liquids, gases, slurries, swaging, electrostatic bonding, embedding by polymer polymerization, embedding by pulse plasma polymerization, encased within a liposome for oral, intravenous, transdermal, subcutaneous, or other means of delivery, contained integrally within the structure of a microspherical semiconductor serving other purposes, including one of drug delivery reservoir, biosensor and temperature sensor; and entrapping the transponder segments with an attachment layer, and wherein in response to said electromagnetic signal being transmitted to a select one of said one or more transponders, an RF signal is modulated with said data to emit said data from said select one of said one or more transponders using said RF signal, and wherein said modulated RF signal is received externally of said one or more transponders and the object.

* * * * *